(12) United States Patent
Stout

(10) Patent No.: US 11,744,452 B1
(45) Date of Patent: Sep. 5, 2023

(54) INTRA-ORAL SCANNING AND IMAGE ACQUISITION MODULE

(71) Applicant: Matthew M. Stout, Chappaqua, NY (US)

(72) Inventor: Matthew M. Stout, Chappaqua, NY (US)

(73) Assignee: APOLLO INNOVATIONS, LLC

( * ) Notice: Subject to any disclaimer, the term of this patent is extended or adjusted under 35 U.S.C. 154(b) by 0 days.

(21) Appl. No.: 18/131,020

(22) Filed: Apr. 5, 2023

(51) Int. Cl.
| | |
|---|---|
| *A61B 6/00* | (2006.01) |
| *A61B 1/247* | (2006.01) |
| *A61B 1/00* | (2006.01) |
| *A61B 1/06* | (2006.01) |

(52) U.S. Cl.
CPC .......... *A61B 1/247* (2013.01); *A61B 1/00096* (2013.01); *A61B 1/00128* (2013.01); *A61B 1/0684* (2013.01)

(58) Field of Classification Search
CPC . A61B 1/247; A61B 1/00096; A61B 1/00128; A61B 1/0684
See application file for complete search history.

(56) References Cited

U.S. PATENT DOCUMENTS

| | | | |
|---|---|---|---|
| 6,908,307 B2 | 6/2005 | Schick | |
| 9,060,108 B1 | 6/2015 | Kuffner | |
| 9,154,677 B2 | 10/2015 | Merz | |
| 9,939,714 B1 | 4/2018 | Matthews | |
| 9,967,543 B2 * | 5/2018 | Yun | A61B 1/247 |
| 10,855,894 B2 | 12/2020 | Biasini et al. | |

(Continued)

FOREIGN PATENT DOCUMENTS

| | | |
|---|---|---|
| CN | 108471938 | 7/2017 |
| CN | 207638761 | 7/2018 |
| CN | 216981942 | 7/2022 |

OTHER PUBLICATIONS

Hartley Charlton, "Apple Moving Forward With Plans for 'Folded' Periscope Cameras to Significantly Increase iPhone's Optical Zoom", Nov. 30, 2020, https://www.macrumors.com/2020/11/30/apple-moving-forward-with-periscope-cameras/.

*Primary Examiner* — Howard D Brown, Jr.
(74) *Attorney, Agent, or Firm* — Lawrence B. Goodwin; Mandelbaum Barrett PC

(57) ABSTRACT

An intra-oral scanning and image data module comprises a housing having a distal and proximal end, a first aperture proximate to the distal end, and a second aperture proximate to the proximal end. The housing contains a first mirror angled at 45° relative to the first aperture and a second mirror angled at 45° relative to the second aperture. The first and second mirrors are angled relative to each other such that light entering the first aperture is redirected to exit the second aperture. A securement mechanism is connected to the housing, located proximate to the second aperture, and adapted to facilitate a connection of the scanning and image data module to a smart device. A light source is located proximate the distal end. Preferably, the light source is powered by the smart device and is connected to the housing. The module may further comprise an optical lens cartridge disposed within the housing and containing one or more lenses adapted to modify the optical properties of the light entering the first aperture.

19 Claims, 4 Drawing Sheets

(56) References Cited

U.S. PATENT DOCUMENTS

| | | | |
|---|---|---|---|
| 2007/0015969 A1* | 1/2007 | Feldman | A61B 5/0084 |
| | | | 600/160 |
| 2008/0082000 A1* | 4/2008 | Thoms | A61B 1/00177 |
| | | | 600/476 |
| 2011/0081946 A1 | 4/2011 | Singh | |
| 2011/0208004 A1* | 8/2011 | Feingold | G02B 6/4215 |
| | | | 600/178 |
| 2014/0015928 A1* | 1/2014 | Koinig | G03B 35/08 |
| | | | 348/45 |
| 2015/0257636 A1* | 9/2015 | Kohler | A46B 15/0036 |
| | | | 433/29 |
| 2015/0264238 A1 | 9/2015 | Hurst et al. | |
| 2016/0191901 A1* | 6/2016 | Stegall | H04N 23/56 |
| | | | 348/49 |
| 2021/0286157 A1 | 9/2021 | Eromaki | |
| 2022/0196961 A1 | 6/2022 | Suzuki et al. | |

\* cited by examiner

INTRA-ORAL SCANNING AND IMAGE ACQUISITION MODULE

FIELD OF THE INVENTION

The present invention is directed the field of scanning and anatomical image data acquisition devices, in particular, intra-oral image acquisition devices.

BACKGROUND OF THE INVENTION

Clinicians in the dental industry need to clearly visualize a patient's dental anatomy to aid in the patient's treatment. Dental cameras may be used for this purpose as well as to capture images to archive for later retrieval, to potentially transfer such images to other clinicians, and to provide the patient with a visual understanding of the patients' clinical options.

Dental cameras typically comprise special purpose hardware and software for providing power, lighting, image sensing, optics, video processing, storage and communication capabilities. Such special purpose hardware and software can be expensive and subject to rapid obsolescence as image sensing, video processing, storage and communications technologies evolve.

In an attempt to improve upon the technology, U.S. Pat. No. 9,939,714 seeks to leverage the continuously improving video processing technology provided by today's mobile phones. In that patent, a periscope module is aligned with and attached to a camera lens of a mobile phone via a mounting ring secured to the phone. The periscope module is adapted to be inserted into the patient's mouth and images captured by the module are directed to the camera lens. The module also includes a light tube aligned with and attached at one end to the light source of the mobile phone and adapted to illuminate the subject.

Although the foregoing approach attempts to leverage the improving technology provided by modern mobile phone developments, it does so at the expense of simplicity and flexibility, as the module requires a complicated arrangement requiring the attachment of mounting rings for the periscope and light tube. Furthermore, and significantly, such arrangement requires the precise alignment between the periscope and light tube, on the one hand, and the phone optics and light source on the other. The apparatus therefore has limited applicability from phone to phone, as the periscope and light tube of the apparatus need to accommodate the specific arrangement, size and layout of the phone optics and light source, so that apparatus specifically designed for one model of mobile phone likely will not accommodate a later model of phone, even from the same manufacturer, thus requiring different sets of apparatus to accommodate different phones.

SUMMARY OF THE INVENTION

Accordingly, the present invention is directed to an anatomical, and in particular, intra-oral scanning and image data acquisition module that can be attached to a variety of smart devices such as mobile phones, tablets, etc., of varying brands, models, designs and specifications, for capturing images for use in medical, and in particular, dentistry and dental specialties, for diagnosis, treatment planning, fabrication of pertinent patient appliances and the direction of clinical care delivery. The module has a multi-piece modular design that integrates with a native smart-device camera hardware to access a dental image in a manner that could not be accessed through the use of the native camera hardware on its own. The module can be applied to smart devices of different manufacturers, and across product lines of the same manufacturer. The module attaches to the external surface of smart devices with an extension that contains an aperture applied to a native camera, internal light redirection optics, an aperture to the subject, an interchangeable optical lens cartridge, and a separate, independent light source powered by the smart device. The module contains an adjustable strap to adapt to the size, shape, and contours of the smart device to appropriately affix the imaging device for use.

Although the primary application of the present invention is in the field of dentistry, the invention may find additional applicability in other fields as well, to scan and image other body parts.

In accordance with a first aspect of the invention, an intra-oral scanning and image data module comprises a housing having a distal and proximal end, a first aperture proximate to the distal end, and a second aperture proximate to the proximal end. The housing contains a first mirror angled at 45° relative to the first aperture and a second mirror angled at 45° relative to the second aperture. The first and second mirrors are angled relative to each other such that light entering the first aperture is redirected to exit the second aperture. A securement mechanism is connected to the housing, located proximate to the second aperture, and adapted to facilitate a connection of the scanning and image data module to a smart device. A light source is located proximate the distal end. Preferably, the light source is powered by the smart device and is connected to the housing. The module preferably includes a power cord, a portion of which is disposed within the housing, the power cord connected at one end to the light source and at another end to a connector adapted to connect to the smart device. The light source is preferably an LED.

The module may further comprise an optical lens cartridge disposed within the housing and containing one or more lenses adapted to modify the optical properties of the light entering the first aperture. Preferably, the housing and the optical lens cartridge are configured such that an optical lens cartridge having first optical properties can be removed from the housing and replaced by another optical lens cartridge having second optical properties different from the first optical properties. The optical lens cartridge may include identifying indicia, such as an NFC or RFID device, adapted to communicate with the smart device and identify its optical properties.

The module may further include an interchangeable sleeve having an aperture conforming to the first aperture and adapted to fit over the distal end of the housing. The distal end of the housing and/or the interchangeable sleeve may include measurement indicia. Preferably, the securement mechanism comprises a strap affixed to one side of the housing and a loop affixed to an opposite side of the housing, the strap adapted to be threaded through the loop.

In accordance with a second aspect of the invention, an appliance for facilitating the examination of a patient's anatomy comprises an appliance housing having a first end adapted to be attached to a device having a camera lens and a second end adapted to be directed to the anatomy of a patient, a combination of mirrors arranged so that images from the second end are translated to the first end and the camera lens when the housing is attached to the device, and a light source disposed in the second end of the housing for illuminating the patient's anatomy, the light source having a power cord adapted to be connected to the device to thereby power the light source. The appliance may include a compartment adapted to receive a lens cartridge for modifying the images from the second end, and a lens cartridge adapted to be inserted into the compartment. Preferably, a strap, sized to allow the application of the first end to a smart phone, is attached to the housing and facilitates the application of the first end to the device. The second end of the appliance may be sized to allow it to be inserted into a patient's mouth.

BRIEF DESCRIPTION OF THE DRAWINGS

These and other objects and aspects of the present invention will be described with reference to the following drawing figures, of which.

DETAILED DESCRIPTION

Figure 1A:
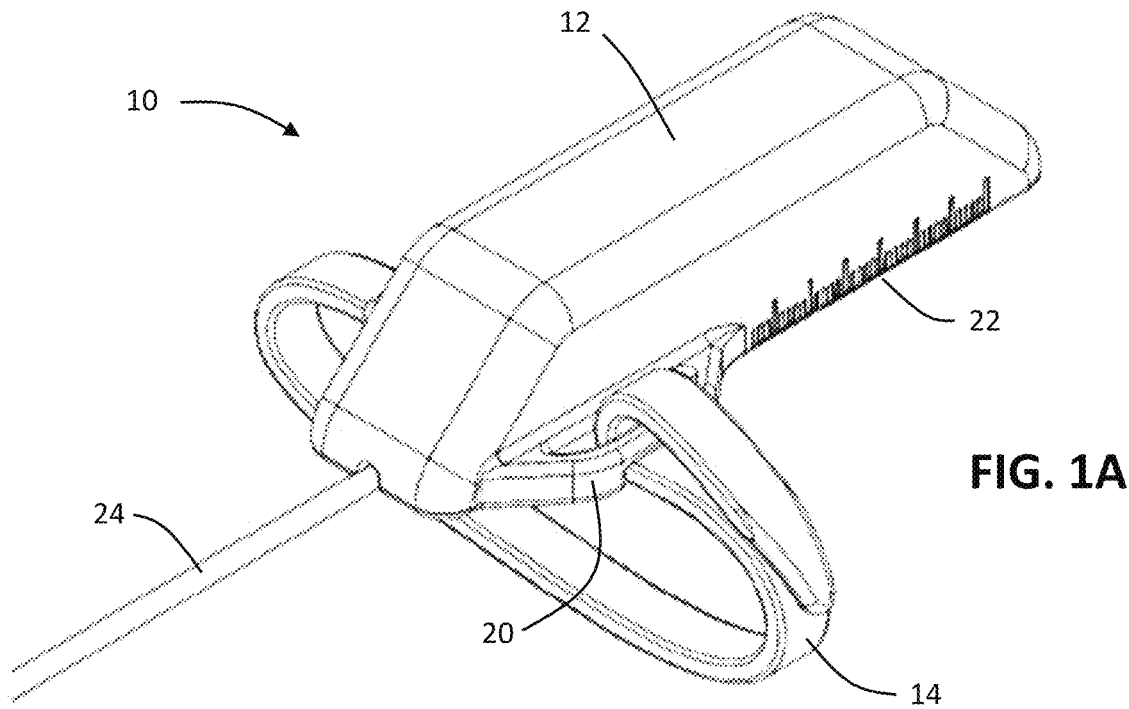
FIG. 1A is a perspective view of the top of an example of an intra-oral scanning and image data acquisition module in accordance with the present invention.
Figure 1B:
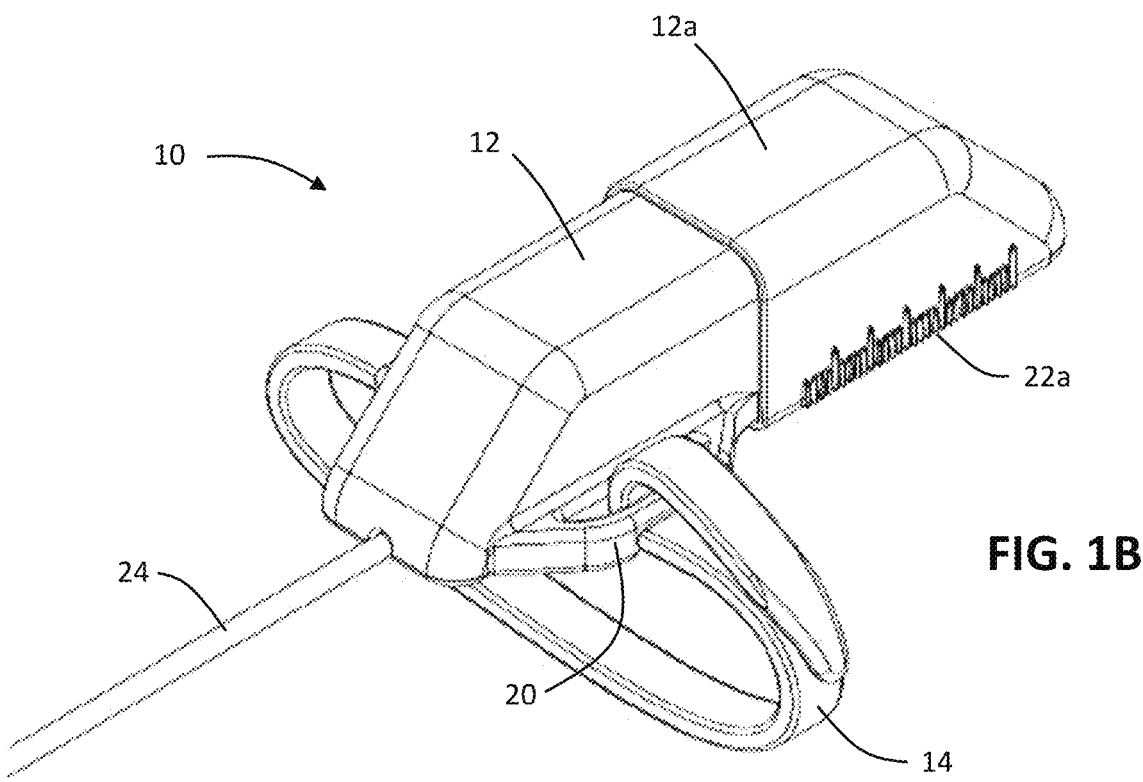
FIG. 1B is a perspective view of the intra-oral scanning and image data acquisition module of FIG. 1A having an interchangeable sleeve that fits over the end of the module.
Figure 2A:
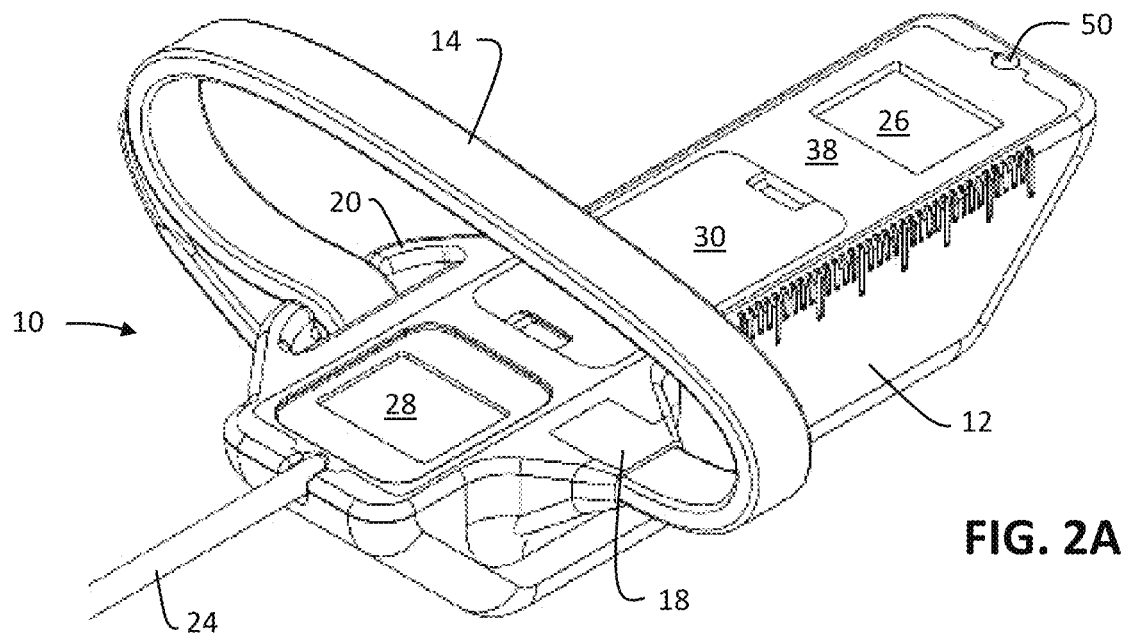
FIGS. 2A and 2B are perspective views of the bottom of an example of an intra-oral scanning and image data acquisition module in accordance with the present invention.
Figure 2B:
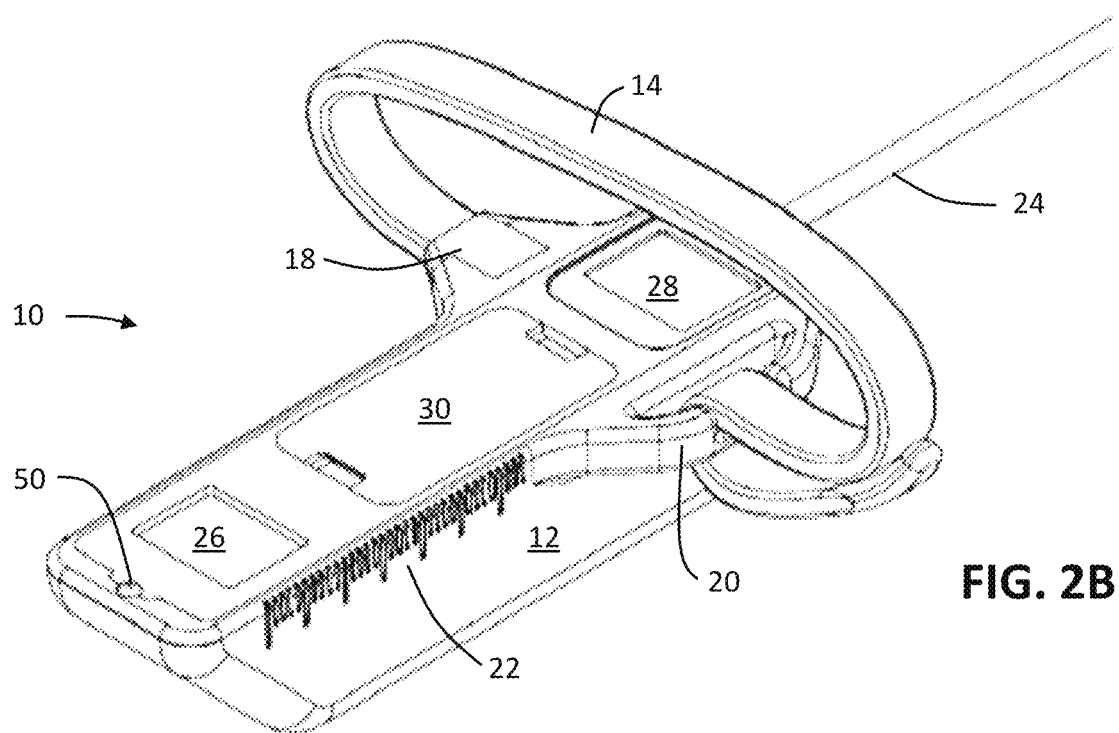
Figure 3A:
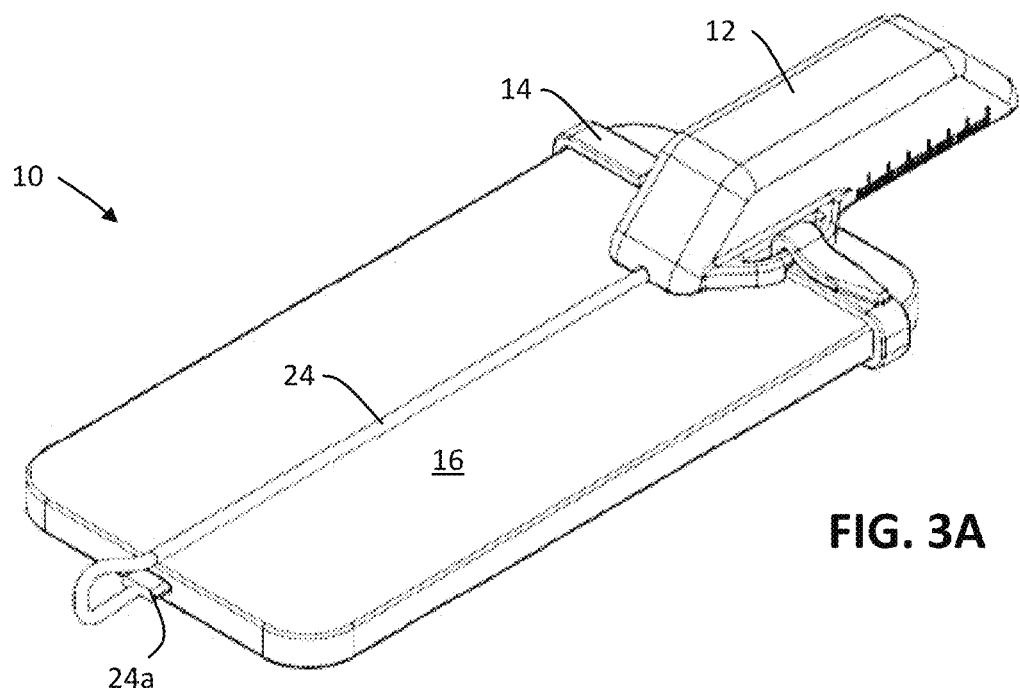
FIGS. 3A and 3B are perspective views of an example of an intra-oral scanning and image data module in accordance with the present invention applied to a smart phone.
Figure 3B:
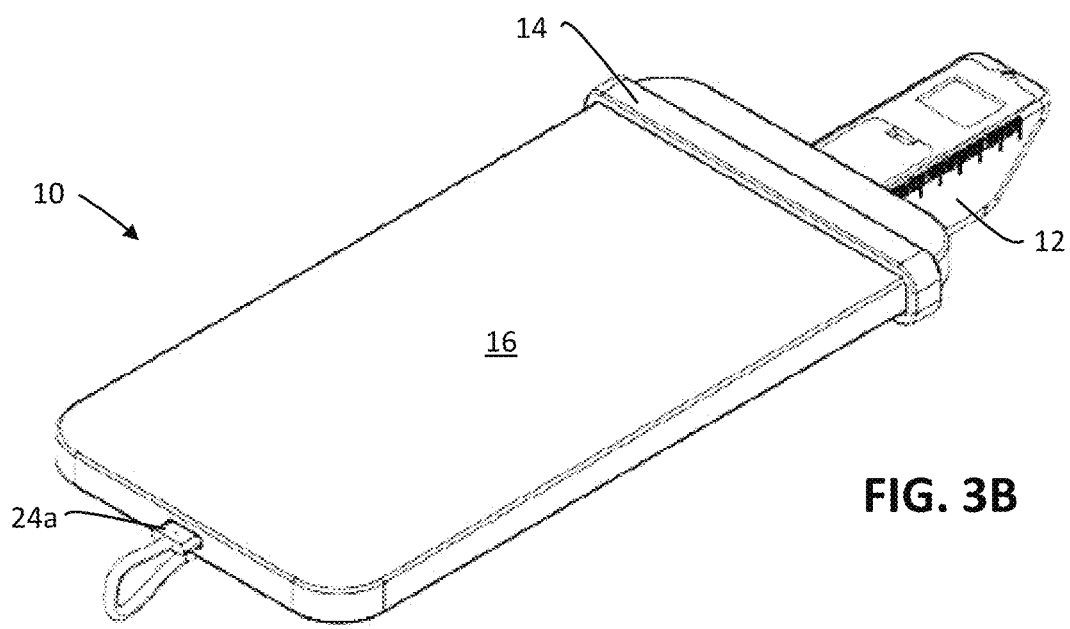

With first reference to FIGS. 1A-1B, 2A-2B, and 3A-3B, an example of an image acquisition module 10 of the present invention includes a housing 12 and flexible strap 14 which facilitates the application of the module to a smart device 16, such as a smart phone or tablet. The strap 14, which can be adapted and sized to fit smart device 16, is located at the proximal end of the housing 12 and is secured to the housing at one end at connection point 18, best shown in FIGS. 2A and 2B. On the other side of the housing 12, opposite of the connection point 18, is a loop 20 through which the other end of the strap 14 is inserted and tightened for securing the strap—and the module 12—to the smart device 16, as shown in FIGS. 3A and 3B. The end of the strap can be secured to the strap along its length by any suitable expedient, for example, Velcro®, interlocking ratchet straps, or embedded, complementary magnets in the tip of the strap and along its length that engage each other, to provide secure retention of the housing to the smart device. The strap 14 may be sized to accommodate a variety of sizes and configurations of smart devices, so that it can be affixed to, and make intimate contact with, numerous types of smart devices 16.

The distal end of housing 12 may be provided with graduated millimeter or other measurement indicia 22. Additionally, interchangeable sleeves 12a, FIG. 1B, that fit over distal end of the housing, may also be provided to allow the use of the module with multiple patients in rapid succession. Such sleeves will have an aperture conforming to the configuration of aperture 26. Preferably, the interchangeable sleeves will also have measurement indicia 22a.

The module 10 is also provided with a power cord 24 for supplying power to an LED located at the distal end of the module, as will be described below.

With reference to FIGS. 2A and 2B, the underside of the module is provided with a distal aperture 26, which in use is positioned within the patient's mouth, and a proximal aperture 28, which is positioned over the native camera lens of the smart device, to provide an optical path between the patient's mouth and the native camera, as will be described. The underside of the module is also provided with a cover 30 for an optical lens cartridge, as will also be described. The apertures may be sized and shaped to accommodate a variety of sizes and configurations of smart device cameras, so that the module can be used with many different devices, the primary requirement being that the proximal aperture 28 cover the lens of the camera on the smart device.

The components of the module and operation thereof will be described with reference to FIGS. 4 and 5. A chassis 32, adapted to be contained within the housing 12, may be provided for precise mounting of internal components as will be described. As best shown in FIG. 5, the housing 12 and chassis 32, in cross-section, are provided with sidewalls angled at 45° and mirrors 36a and 36b, to produce an optical path between distal and proximal apertures 26 and 28 as shown by the dashed line in FIG. 5, in a manner similar to a periscope. A chassis cover 38 is provided on the chassis 32 and has openings defining the apertures 26 and 28. Preferably, protective lenses 40a and 40b are secured to the chassis cover 38 to protect the internal portions of the module.

Figure 4:
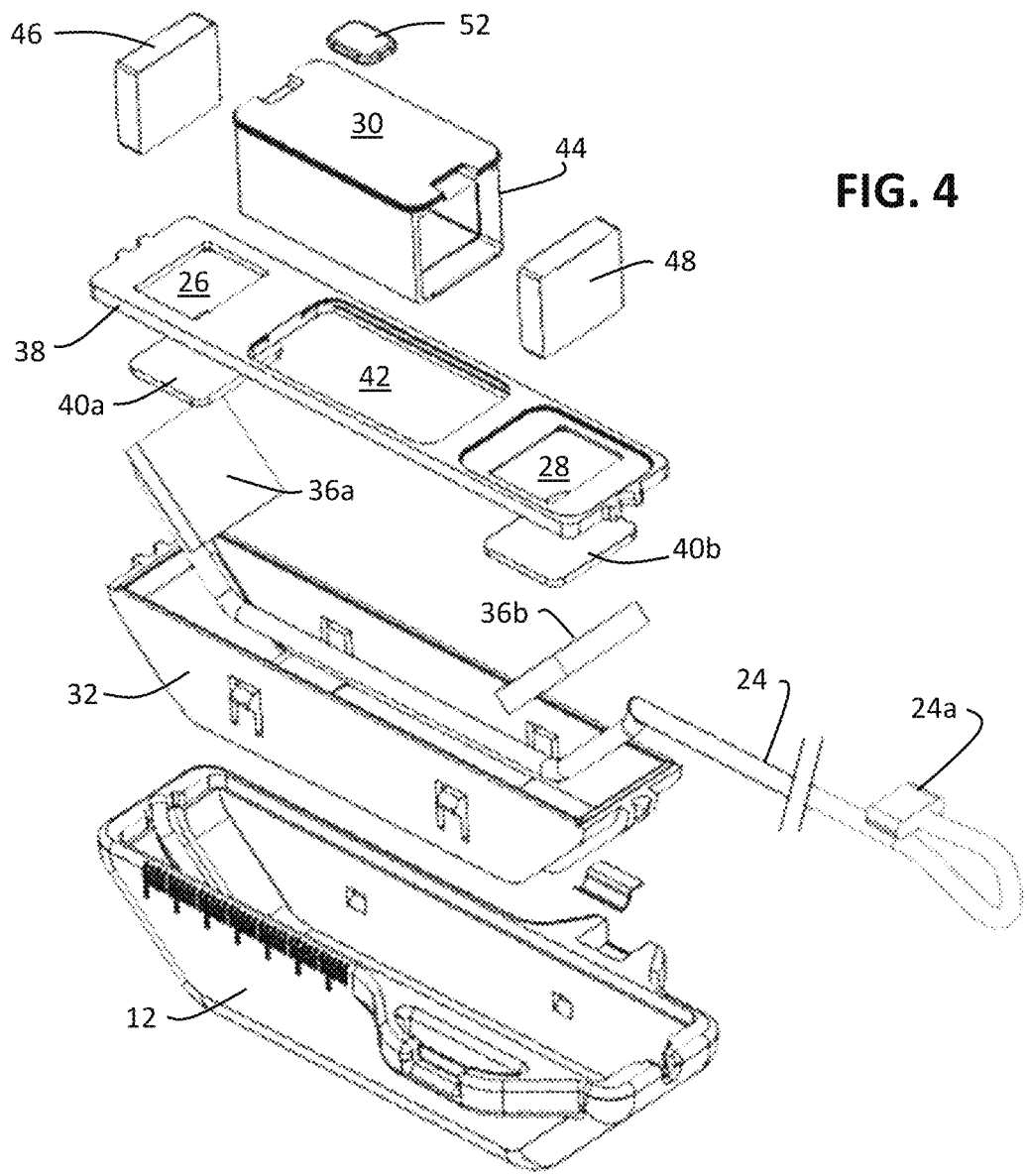
FIG. 4 is an exploded perspective view of the components of an example of an intra-oral scanning and image data module in accordance with the present invention.
Figure 5:
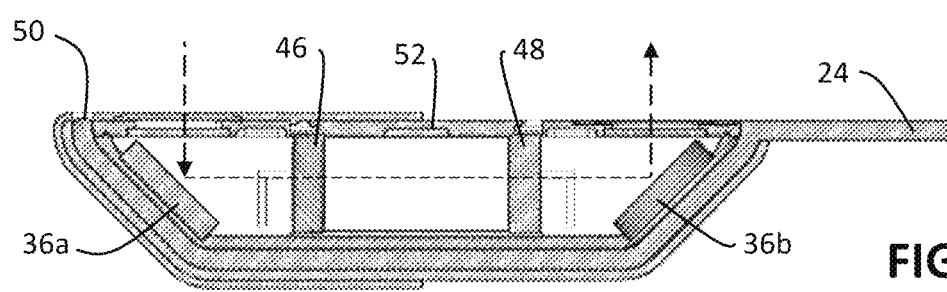
FIG. 5 is a cross-sectional view of the components of an example of an intra-oral scanning and image data acquisition module in accordance with the present invention.

As best shown in FIG. 4, the chassis cover 38 is also provided with an aperture 42 to allow the insertion and removal of an optical lens cartridge 44 into the chassis, within the optical path shown in FIG. 5. The optical lens cartridge 44 is adapted to contain one or more lenses 46, 48, such that different optics can be interchangeably used by swapping out one lens cartridge 44, having one set of optical properties, for another lens cartridge having different optical properties, to alter image capturing capabilities of the module, to provide clarity, focus and sharpening to enhance the quality of the captured image, as desired. For example, specific optical lens/cartridge options may include optics optimized for specific makes and models of smart devices, or for adults, children, standard macro/telephoto/ fisheye/ wide angle or other magnifications. Alternatively, individual lenses may be selectively inserted into the chassis 32 or cartridge 44, rather than swapping out an entire cartridge. If desired, the specific cartridge in use can be communicated to an application running on the smart device by using an NFC (near field communication) or RFID (radio frequency identification) device 52 capable of communicating with the smart device, to optimize the capabilities of the system under a variety of conditions. Alternatively, the lens cartridge can be identified by using a serialized sticker and/or barcode having a cartridge identifier.

As best shown in FIGS. 2A and 2B, an LED 50 is located at the distal end of the module. Power cord 24, which is adapted to be connected to the USB or iPhone® port of the smart device via connector 24a, FIGS. 3A-3B and 4, provides power from the smart device to the LED. Alternatively, the LED can be co-located with or near the connector 24a, and an optical fiber can be used in place of power cord 24. Thus, the module 12 has its own illumination source and does not require alignment of the module relative to the illumination source of the smart device.

In operation, the clinician may select and insert into the module a preferred optical lens cartridge for a particular patient and a particular smart device, as described above. The clinician will then align the proximal aperture 28 with the native camera optics of the smart device, and secure the module to the device by using the strap 14 and loop 20, as described. The connector 24a will be inserted into the connector port of the smart device to provide power to the LED 50. The clinician will also activate a suitable application to run on the smart device which will recognize the particular lens cartridge being used, by recognizing the NFC or RFID chip on the lens cartridge, for example, so that the application may optimize the optical processing for the specific lens cartridge. The clinician will then insert the distal end of the module into the patient's mouth and record photos and/or videos of the patient's teeth and surrounding anatomy. The application may also provide a platform for further processing, for example, photo stitching. Still further, the present invention can be used with smart devices that produce depth of field and 3-D images of the patient's anatomy, for example, through the use of LIDAR or the like.

Thus, due to the use of a separate light source, independent of the light source of the smart device, and the use of the flexible strap 14, the module does not have to be manufactured and configured to any specific type of smart device, but instead may be used with a large variety of different smart devices of different manufacturers and different models within the same manufacturer, to provide high-quality imaging with a single "universal" module.

The examples disclosed herein are for exemplary purposes only and should not be construed as limiting the present invention, which is defined in the following claims. For example, the apparatus in accordance with the present invention may have general applicability not only to dentistry, but to other parts of a patient's anatomy as well.

I claim:

1. An intra-oral scanning and image data module comprising:
    a) a housing having a distal and proximal end, a first aperture proximate to said distal end, and a second aperture proximate to said proximal end, said housing containing
        i) a first mirror angled at 45° relative to said first aperture;
        ii) a second mirror angled at 45° relative to said second aperture;
    b) said first and second mirrors angled relative to each other such that light entering said first aperture is redirected to exit said second aperture;
    c) a securement mechanism connected to said housing, located proximate to said second aperture, and adapted to facilitate a connection of said scanning and image data module to a smart device; and
    d) a light source located proximate said distal end.

2. The intra-oral scanning and image data module of claim 1 wherein said light source is powered by said smart device.

3. The intra-oral scanning and image data module of claim 2 wherein said light source is connected to said housing.

4. The intra-oral scanning and image data module of claim 3 further comprising a power cord a portion of which is disposed within said housing, said power cord connected at one end to said light source and at another end to a connector adapted to connect to said smart device.

5. The intra-oral scanning and image data module of claim 4 wherein said light source is an LED.

6. The intra-oral scanning and image data module of claim 1 further comprising an optical lens cartridge disposed within said housing and containing one or more lenses adapted to modify the optical properties of said light entering said first aperture.

7. The intra-oral scanning and image data module of claim 6 wherein said housing and said optical lens cartridge are configured such that an optical lens cartridge having first optical properties can be removed from said housing and replaced by another optical lens cartridge having second optical properties different from said first optical properties.

8. The intra-oral scanning and image data module of claim 7 wherein said optical lens cartridge includes identifying indicia adapted to communicate with said smart device and identify its optical properties.

9. The intra-oral scanning and image data module of claim 8 wherein said identifying indicia are contained in an NFC or RFID device.

10. The intra-oral scanning and image data module of claim 1 further comprising an interchangeable sleeve having an aperture conforming to said first aperture and adapted to fit over said distal end of said housing.

11. The intra-oral scanning and image data module of claim 1 wherein said distal end of said housing includes measurement indicia.

12. The intra-oral scanning and image data module of claim 10 wherein said interchangeable sleeve includes measurement indicia.

13. The intra-oral scanning and image data module of claim 1 wherein said securement mechanism comprises a strap affixed to one side of said housing and a loop affixed to an opposite side of said housing, said strap adapted to be threaded through said loop.

14. An appliance for facilitating the examination of a patient's anatomy, comprising:
    a) an appliance housing having a first end adapted to be attached to a device having a camera lens and a second end adapted to be directed to the anatomy of a patient;
    b) a combination of mirrors arranged so that images from said second end are translated to said first end and said camera lens when said housing is attached to said device; and
    c) a light source disposed in said second end of said housing for illuminating said patient's anatomy, said light source having a power cord adapted to be connected to said device to thereby power said light source.

15. The appliance of claim 14 wherein said housing includes a compartment adapted to receive a lens cartridge for modifying said images from said second end.

16. The appliance of claim 15 further comprising a lens cartridge adapted to be inserted into said compartment.

17. The appliance of claim 14 further comprising a strap attached to said housing for facilitating the application of said first end to said device.

18. The appliance of claim 17 wherein said strap is sized to allow the application of said first end to a smart phone.

19. The appliance of claim 18 wherein said second end is sized to allow it to be inserted into a patient's mouth.

* * * * *